United States Patent [19]

Snow et al.

[11] Patent Number: 4,986,922

[45] Date of Patent: Jan. 22, 1991

[54] SOFTENING COMPOSITIONS INCLUDING QUATERNARY AMMONIUM FUNCTIONAL SILOXANES

[75] Inventors: Steven A. Snow; Linda M. Madore, both of Midland, Mich.

[73] Assignee: Dow Corning Corporation, Midland, Mich.

[21] Appl. No.: 504,484

[22] Filed: Apr. 4, 1990

[51] Int. Cl.$^5$ ............... C06M 13/322; C06M 13/513; C06M 1/62; C07F 7/10
[52] U.S. Cl. ................................. 252/8.8; 252/8.9; 252/174.15; 252/357; 556/425
[58] Field of Search ............ 252/8.6, 8.8, 8.9, 174.15, 252/357; 556/425

[56] References Cited

U.S. PATENT DOCUMENTS

| | | | |
|---|---|---|---|
| 3,624,120 | 11/1971 | Yetter .................................. | 556/425 |
| 3,661,964 | 5/1972 | Griffiths et al. ..................... | 556/425 |
| 4,006,176 | 2/1977 | Heckert et al. ...................... | 252/174.15 |
| 4,699,988 | 10/1987 | Traver et al. ........................ | 556/425 |
| 4,784,799 | 11/1988 | Petroff ................................. | 252/174.15 |
| 4,879,051 | 11/1989 | Lo et al. .............................. | 252/174.15 |
| 4,918,210 | 4/1990 | Fenton et al. ....................... | 252/357 |

FOREIGN PATENT DOCUMENTS 1006729 4/1964 United Kingdom .
1549180 7/1976 United Kingdom .

OTHER PUBLICATIONS

Snow et al., Synthesis and Characterization of Zwitterionic Silicone Sulfobetaine Surfactants, Langmuir 6(2), pp. 385–391, 1990.

Primary Examiner—A. Lionel Clingman
Assistant Examiner—J. E. Darland
Attorney, Agent, or Firm—Jim L. DeCesare

[57] ABSTRACT

A fabric softener including a silicon compound having the formula

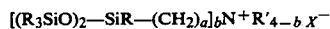

wherein R is an alkyl radical having one to six carbon atoms; R' is an alkyl or aryl radical having one to eighteen carbon atoms; X is chloride, bromide, iodide, nitrate, or $RSO_4^-$; a is an integer having a value from one to ten; and b is an integer having a value of two or three.

22 Claims, No Drawings

SOFTENING COMPOSITIONS INCLUDING QUATERNARY AMMONIUM FUNCTIONAL SILOXANES

BACKGROUND OF THE INVENTION

This invention relates to a fabric softening composition which includes a mixture of a quaternary ammonium functional siloxane and at least one surfactant which is anionic. The invention is also directed to detergent laundering products containing the fabric softening composition.

Solid detergent formulations are sold in powder or granular form. A disadvantage of solid detergents is that, on account of the hygroscopic nature of individual raw materials of the formulation, the solid detergent shows a pronounced tendency towards caking or clumping in the presence of small quantities of moisture. This does not make the detergent unusable, however, because the effect of the individual components of the detergent remain intact even after clumping or caking in the presence of moisture. However, the appearance of the detergent in most cases is diminished. As a result, there has been a desire to develop liquid detergent compositions for convenience in lieu of conventionally formulated solid detergent compositions. The liquid detergent allows for use of lower washing temperatures inclusive of cold water laundering. Granular detergents have not fully adapted to such variations because of weaknesses in respect of dissolving speed, insolubility, and cleaning efficiency. Due to such problems of caking and the slowness of solid and granular detergents to dissolve, trends in detergent manufacture have leaned toward the liquid detergent. Such detergents usually include one or more anionic, nonionic, and cationic organic surfactants, water, brightening agents, hydrotropes, enzymes, soil suspending agents, bleaches, pH modifiers, and solvents. It is not uncommon to also include antifoam formulations as a part of the detergent package. Such systems may be built or free of builders.

A fabric softener, on the other hand, often contains a dilute solution or dispersion of a quaternary ammonium derivative used to treat fabrics in the final rinse cycle of a laundering process in order to make the fabrics feel softer. In addition to softness, fabric softeners are known to also provide static control. Because of the affinity of quaternary ammonium compounds for negatively charged surfaces, their single largest market has been as fabric softeners. Commercial fabric softeners generally include about a four to eight percent dispersion of quaternary ammonium compound which is added to the rinse cycle of the washing process. In some cases, a fatty acid stearate is added to modify the handle. The quaternary ammonium compound can also be applied to a nonwoven sheet or a polyurethane foam which is added with wet clothes in a dryer. Such sheets contain a fatty amine or a fatty acid ester which allows the quaternary ammonium compound to transfer from the sheet to the clothes in the dryer during the drying cycle. Recently, there have been devised combined detergent and softener formulations which allow introduction of all additives in the wash cycle.

A basic distinction should be drawn between a rinse cycle softener and a wash cycle softener. As noted hereinabove, the rinse cycle fabric softener is a liquid dispersion of a quaternary ammonium compound which is added separately to the rinse liquor during the rinse cycle of the laundering device. A wash cycle fabric softener in contrast typically contains the quaternary ammonium compound which is mixed in with the laundry detergent and added to the wash liquor by the homemaker before initiation of the wash cycle of the fabric laundering device.

Quaternary ammonium functional siloxanes are not new in the art. For example, in United Kingdom Pat. No. 1,549,180, published July 25, 1979, there is described certain fabric conditioning compounds which are dialkylquaternary ammonium terminated linear polydimethylsiloxanes. The compounds of the present invention, in contrast, are monoquaternary ammonium functional polydimethylsiloxanes, and are trialkylsiloxy terminated rather than dialkylquaternary ammonium terminated as the materials in the '180 patent. United Kingdom Pat. No. 1,006,729, published Oct. 6, 1965, is directed to certain surfactants which are trialkyl mono(polysiloxy) ammonium chlorides. However, the compounds of the present invention can be distinguished in that the compounds are dialkyl di(polysiloxy) ammonium chlorides, as well as some species which are monoalkyl tri(polysiloxy) ammonium chlorides. Thus, it should be apparent that the present invention includes new and novel compositions of matter and uses thereof not previously known in the prior art.

SUMMARY OF THE INVENTION

This invention relates to a compound having the formula

or

wherein R is an alkyl radical having one to six carbon atoms; R' is an alkyl or aryl radical having one to eighteen carbon atoms; R" is hydrogen or R'; X is chloride, bromide, iodide, nitrate, or $RSO_4^-$; a is an integer having a value from one to ten; and b is an integer having a value of two or three.

The invention also is directed to a softening composition including a compound having the formula

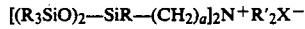

or

wherein R is an alkyl radical having one to six carbon atoms; R' is an alkyl or aryl radical having one to eighteen carbon atoms; R" is hydrogen or R'; X is chloride, bromide, iodide, nitrate, or $RSO_4^-$; and a is an integer having a value from one to ten.

A particularly preferred species of the compound comprehended under the foregoing genus is the compound $[(Me_3SiO)_2SiMe(CH_2)_3]_2N^+Me_2I^-$ wherein Me is methyl.

These and other features, objects, and advantages of the herein described present invention will become more readily apparent when considered in light of the detailed description of the invention which follows.

DETAILED DESCRIPTION OF THE INVENTION

Ammonium compounds in which all of the hydrogen atoms on nitrogen have been substituted by alkyl groups are called quaternary ammonium salts. These compounds may be represented in a general sense by the formula:

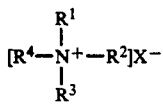

The nitrogen atom includes four covalently bonded substituents that provide a cationic charge. The R groups can be any organic substituent that provides for a carbon and nitrogen bond with similar and dissimilar R groups. The counterion X is typically halogen or alkyl sulfates. Use of quaternary ammonium compounds is based on the hydrophilic portion of the molecule which bears a positive charge. Since most surfaces are negatively charged, solutions of these cationic surface active agents are readily adsorbed to the negatively charged surface.

The compounds of the present invention are of the foregoing type, and can be more particularly illustrated by the formula

wherein R is an alkyl radical having one to six carbon atoms; R' is an alkyl or aryl radical having one to eighteen carbon atoms; R" is hydrogen or R'; X is chloride, bromide, iodide, nitrate, or $RSO_4^-$; a is an integer having a value from one to ten; and b is an integer having a value of two or three. These quaternary ammonium functional siloxanes are monoquaternary ammonium functional polydimethylsiloxanes, and are trialkylsiloxy terminated. The compounds of the present invention can also be described as dialkyl di(polysiloxy) ammonium chlorides when the integer a is two, as well as some species which are monoalkyl tri(polysiloxy) ammonium chlorides when the integer a is three. The dialkyl di(polysiloxy) ammonium chloride species is preferred, and especially the particular compound $[(Me_3SiO)_2SiMe(CH_2)_3]_2N^+Me_2I^-$ wherein Me is methyl.

As is well known, water has a surface tension of approximately seventy-two dynes per centimeter. It has been found that solutions containing as little as 0.001 percent by weight of the compounds of the present invention possess a surface tension of about sixty dynes per centimeter, and those containing about one percent by weight have a surface tension of the order of about twenty dynes per centimeter. The compounds of the present invention can be used as additives in liquid detergents, cleaners, and automatic dishwashing detergents, and find application as ingredients in powdered detergents for fabric washing machines. These compounds can also be employed as additives in wash cycle softeners and as ingredients in rinse cycle softeners. In addition, the compound have utility as antistatic agents particularly in wash cycle laundry detergent formulations. The softening effects achieved by the addition of the compounds of the present invention can be enhanced by mixing the compounds with one or more anionic surfactants such as linear alkylbenzene sulfonates, and the compounds may be employed at much lower use levels in comparison to conventional commercial organic based fabric softeners. Reductions as much as fifty to seventy-five percent is not uncommon with the cationic quaternary ammonium functional siloxanes of the present invention.

These novel, cationic, silicone surfactants are prepared with two instead of one siloxane group attached to a quaternary ammonium functional nitrogen atom. This is accomplished by the following series of steps:

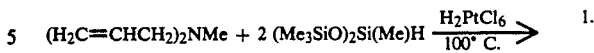

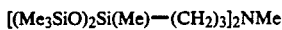

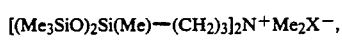

where X is Cl, Br, I, or $MeSO_4$.

These compounds are crystalline solids which have varying melting points and solubilities in water. They can function as potent surfactants, reducing the surface tension of water from 72 to 21 dyne/cm. They also adsorb very efficiently on negatively charged surfaces such as fabrics, skin, and hair. This adsorption allows for a conditioning or softening effect.

The following example is illustrative of a method for the preparation of the compound $[(Me_3SiO)_2SiMe(CH_2)_3]_2N^+Me_2I^-$ wherein Me is methyl.

EXAMPLE I

Three hundred grams of the amine $[(Me_3SiO)_2Si(Me)-(CH_2)_3]_2NMe$ was dissolved in six hundred grams of hexane under nitrogen gas in a two liter flask and heated to reflux. Seventy grams of MeI in fifty grams of hexane was added dropwise to the flask. The product precipitated rapidly. At the conclusion of the dropwise addition, heating of the flask was continued at sixty degrees Centigrade for two hours. The material in the flask was filtered to isolate the crystalline product. One part of the product was mixed with five parts of hexane and the mixture was allowed to sit for about four days in order to leach out any impurities. This mixture was filtered, washed with hexane, and dried under vacuum. The product was characterized by proton nuclear magnetic resonance (NMR) and infrared spectroscopy. The product was identified as the compound $[(Me_3SiO)_2SiMe(CH_2)_3]_2N^+Me_2I^-$ wherein Me is methyl.

While the liquid detergent of the present invention may contain many of the commonly included ingredients such as surfactants, builders, enzymes and enzyme stabilizers, pH modifiers, bleach activators and bleaches, antifoams, anti-redeposition agents, chelants, soil release polymers, dye transfer protectants, zeolite dispersants, water softeners, perfumes, anti-oxidants, and fluorescent brighteners, the essential ingredients for purposes of the present invention are an anionic surfactant, a nonionic surfactant, a carrier fluid, and the softening agent. Water is a suitable carrier although other fluids such as ethanol, isopropanol, butanol, hexanol, and diethylene glycol, may be employed.

The ratio between the anionic surfactant and the nonionic surfactant is 4:1 to 1:4, more preferably from about one to one to about three to one. The detergent should include on a weight basis at least about 0.5-5.0 percent of the silicone fabric softening agent. The silicone is employed in an amount of about 0.05-0.3 percent by weight based on the weight of fabrics being treated.

The liquid detergent contains at least one surfactant and the surfactants preferred for purposes of the present invention are nonionic and anionic surfactants. In nonionic surfactants, for example, there is no charge on the molecule, and the solubilizing groups are ethylene oxide chains and hydroxyl groups. Such nonionic surfactants are compatible with ionic and amphoteric surfactants, and representative of nonionic surfactants are, for example, polyoxyethylene or ethoxylate surfactants such as alcohol ethoxylates and alkylphenol ethoxylates. Carboxylic acid ester nonionic surfactants include glycerol esters, polyoxyethylene esters, anhydrosorbitol esters, ethoxylated anhydrosorbitol esters, natural fats, oils, and waxes, and ethoxylated and glycol esters of fatty acids. Carboxylic amide nonionic surfactants which may be included are diethanolamine condensates, monoalkanolamine condensates, and polyoxyethylene fatty acid amide. Representative of polyalkylene oxide block copolymer nonionic surfactants are the polyalkylene oxides derived from ethylene, propylene, butylene, styrene, and cyclohexene. Typical of the anionic surfactants that may be employed herein are salts of alkyl sulfates, salts of alkylaryl sulfates, salts of alkyl ether sulfates, salts of alkylaryl ether sulfates, and salts of alkylaryl sulfonates. Exemplary materials included are, for example, alkyl benzene sulfonates, alkyl glyceryl ether sulfonates, alkyl phenol ethylene oxide ether sulfates, esters of alpha-sulfonated fatty acids, 2-acyloxyalkane-1-sulfonic acids, olefin sulfonates, beta-alkyloxyalkane sulfonates, anionic surfactants based on higher fatty acids, and tallow range alkyl sulfates. Both categories of surfactant are well known in the art and are described in more or less detail in U.S. Pat. No. 4,075,118, issued Feb. 21, 1978, for example.

The following examples are set forth in order to illustrate the concepts of the present invention.

EXAMPLE II

In accordance with the present invention, silicones are emulsified in a detergent matrix by first mixing the silicone with the acid form of an anionic surfactant such as a linear alkyl benzene sulfonic acid. The mixture of the anionic surfactant and the silicone was neutralized by the addition of a base such as sodium hydroxide in a mixture of water and ethanol. The salt of the anionic surfactant results from this neutralization. Following completion of the neutralization, the nonionic surfactant was added, together with other optional ingredients such as builders, fatty acids, cationic surfactants, and optical brighteners. The mixture was mechanically agitated in order to insure a homogeneous product. It has been found that in the event that the foregoing procedure is not followed, that the silicone ingredient is caused to separate thus forming an unstable product. This occurs, for example, by the addition of the silicone to a random mixture of various ingredients. In accordance with the present invention, the silicone must be first mixed with an anionic surfactant and neutralized prior to being added to the balance of the liquid detergent formulation in order to provide a stable end product.

The above procedure was followed and formulations of liquid detergent containing a silicone softening agent were prepared. In each instance there was employed thirteen weight percent of an anionic surfactant, thirteen weight percent of a nonionic surfactant, five weight percent of ethanol, two weight percent of silicone softening agent, and the balance being water. The preferred ratio between the anionic surfactant and the nonionic surfactant is 1:1 to 3:1. The anionic surfactant employed was an alkylbenzene sulfonic acid of Vista Chemical Company. The nonionic surfactant was NEODOL ® 25-7, a trademark and product of Shell Chemical Company, Houston, Tex., and a linear primary alcohol. Liquid detergents were prepared containing these ingredients and including the silicone softening agents.

EXAMPLE III

Towels were prepared for treatment by removing the mill textile conditioners applied at the mill during manufacture of the towels. The process was conducted at a commercial laundromat. Bundles of 86:14 cotton polyester terry towels were washed five times with an anionic detergent containing a high level of phosphorus. Detergent remaining in the towels was removed by three final wash and rinse cycles from which detergent was omitted. Each bundle was subjected to eight complete wash and rinse cycles during the stripping process followed by a drying cycle.

The test used to measure softness was a panel test in which from twelve to fifteen people were asked to rank several towels in order of softness. Following treatment, the towels were placed in a constant temperature and humidity room over night to equilibrate, and after which the towels were tested the next day. Dryers tend to overdry towels and provide a harsher feel than normal, and therefore all towels tested in a given panel were conditioned at the same temperature and humidity before testing. Each test included one control towel. The control towel was a towel which had not been treated by a liquid detergent containing a softening agent. The fifteen people were asked to evaluate the towels by feeling the towels and choosing the harshest towel, the softest towel and placing the remaining towels in order of increasing softness. The towels were assigned a ranking between one and six with the highest value corresponding to the softest towel. Before the test was conducted, each member of the panel was asked to wash their hands to remove any residue which might interfere with the test. During the evaluation, the panel members rewashed their hands to remove any softener buildup. Since the softness of a towel increases with repeated handling, a new surface of each towel was exposed for each panel member, and each towel was replaced after evaluation by three people.

EXAMPLE IV

Each of the liquid laundry detergents containing a silicone softening agent as prepared in accordance with Example II was used to treat a fabric bundle which had been conditioned in accordance with the procedure of Example III. The bundles contained six towels and weighed about 1200-1400 grams. The bundle was loaded into a washing machine and about one hundred grams of liquid detergent containing a softening agent was added to the washing machine. The washing machine controls were established to provide a warm water wash (35° C.) and a cold water rinse. The duration of the wash cycle of the particular washing machine employed was about fourteen minutes. At the end of the cycle of the washing machine, the bundle was dried in a dryer for about one hour. Each bundle was exposed to three complete cycles including washing and drying. The bundles were then equilibrated and tested after the first and third cycle to measure softness as indicated in Example III.

The results of the softness test are set forth in Table I hereinbelow. In addition to the silicone softening agents of the present invention, there was also tested softening agents of the prior art for comparative purposes. One softening agent was a commercially employed cationic organic fabric softening agent and a product of Sherex Chemical Company, Dublin, Ohio. The organic softening agent was monohydrogenated tallow trimethylammonium chloride available as a fifty percent by weight active material in isopropanol solvent. This organic softening agent is marketed under the trademark ADOGEN ® 441. The other cationic softening agent tested for comparative purposes was ADOGEN ® 442, also a product and trademark of Sherex, and a dihydrogenated tallow dimethylammonium chloride available as a seventy-five percent by weight active material in isopropanol solvent. Both of the comparative softening agents were not employed in the same amount to treat the fabric bundles as the silicone softening agents of the present invention.

TABLE I

| SOFTENING AGENT IN DETERGENT* | AVERAGE SOFTNESS RANK | |
|---|---|---|
| | FIRST TREATMENT | THIRD TREATMENT |
| (First Series) | | |
| 2% Silicone | 4.0 | 4.1 |
| 4% ADOGEN ® 441 | 1.2 | 1.6 |
| Control** | 3.5 | 3.5 |
| (Second Series) | | |
| 2% Silicone | 5.6 | 4.6 |
| 2% ADOGEN ® 442 | 2.3 | 3.5 |
| Control** | 2.0 | 1.2 |

**Liquid detergent containing 13 weight percent each of anionic and nonionic surfactants; 5 weight percent ethanol; and 69 weight percent water.
*Water content of control reduced to accommodate softening agent.

The table indicates that the silicone provides a significantly higher average softness ranking in comparison to the Control and the corresponding organic softening compositions. In fact, in the "First Series" as shown in the Table, the cationic organic softening agent provided a softening effect less than the Control. This is due to the incompatibility between the cationic organic softening agent and the anionic surfactant present in the detergent. This incompatibility was not noted for the silicone however. Thus, in a typical wash cycle softening detergent, an anionic surfactant is required for cleaning. Where softening is requirement in the wash cycle, a cationic organic surfactant or silicone must be added. In the past, this has proved to be a problem as the anionic and cationic surfactants complex and produce poorer cleaning as well as poorer softening. With the silicone as shown in the Table, this did not prove to be a problem however. In the case of rinse cycle softening, it is common to include cationic surfactants in order to obtain softening benefits. These benefits are often improved by incorporating a silicone in addition to the cationic surfactant. The presence in the rinse cycle of an anionic surfactant is not required as no cleaning is necessary. In fact, it has been previously believed that the presence in the rinse cycle of an anionic surfactant would decrease softening because of complexing with the cationic surfactant as noted. Contrary to this belief, however, and as shown in the "Second Series" in the Table, the combination of the silicone with the anionic surfactant not only did not decrease the softening benefits, but actually caused the softening to improve in comparison to the corresponding organic softening material. This is significant and provides unique and unexpected properties of the softening composition of the present invention including the silicone in combination with an anionic surfactant.

This application is related to copending U.S. application Ser. No. 07/460,794, filed Jan. 4, 1990, entitled "Quaternary Ammonium Functional Siloxanes", and which is assigned to the same assignee as the present application.

It will be apparent from the foregoing that many other variations and modifications may be made in the compounds, compositions, and methods described herein without departing substantially from the essential features and concepts of the present invention. Accordingly, it should be clearly understood that the forms of the invention described herein are exemplary only and are not intended as limitations on the scope of the present invention.

What is claimed is:

1. A softening composition comprising a mixture of at least one surfactant which is anionic and a silicone compound having the formula

$$[(R_3SiO)_2-SiR-(CHR'')_a]_b N^+ R'_{4-b} X^-$$

wherein R is an alkyl radical having one to six carbon atoms; R' is an alkyl or aryl radical having one to eighteen carbon atoms; R" is hydrogen or R'; X is chloride, bromide, iodide, nitrate, or $RSO_4^-$; a is an integer having a value from one to ten; and b is an integer having a value of two or three.

2. The composition of claim 1 in which the compound is $[(Me_3SiO)_2SiMe(CH_2)_3]_2 N^+ Me_2 I^-$ wherein Me is methyl.

3. The composition in accordance with claim 1 including a carrier fluid selected from the group consisting of water, ethanol, isopropanol, butanol, hexanol, propylene glycol, and diethylene glycol.

4. The composition in accordance with claim 1 in which the mixture includes on a weight basis about 0.5 to 5.0 percent of the silicone compound.

5. A softening composition comprising a mixture of at least one surfactant which is anionic and a silicone compound having the formula

$$[(R_3SiO)_2-SiR-(CHR'')_a]_2 N^+ R'_2 X^-$$

wherein R is an alkyl radical having one to six carbon atoms; R' is an alkyl or aryl radical having one to eighteen carbon atoms; R" is hydrogen or R'; X is chloride, bromide, iodide, nitrate, or $RSO_4^-$; and a is an integer having a value from one to ten.

6. The composition of claim 5 in which the compound is $[(Me_3SiO)_2SiMe(CH_2)_3]_2 N^+ Me_2 I^-$ wherein Me is methyl.

7. The composition in accordance with claim 5 including a carrier fluid selected from the group consisting of water, ethanol, isopropanol, butanol, hexanol, propylene glycol, and diethylene glycol.

8. The composition in accordance with claim 5 in which the mixture includes on a weight basis about 0.5 to 5.0 percent of the silicone compound.

9. In a laundry detergent having fabric softening properties and including at least one fabric softening agent, the improvement comprising a silicone fabric softening agent having the formula

$$[(R_3SiO)_2-SiR-(CHR'')_a]_b N^+ R'_{4-b} X^-$$

wherein R is an alkyl radical having one to six carbon atoms; R' is an alkyl or aryl radical having one to eighteen carbon atoms; R" is hydrogen or R'; X is chloride, bromide, iodide, nitrate, or $RSO_4^-$; a is an integer having a value from one to ten; and b is an integer having a value of two or three.

10. The detergent of claim 9 in which the softening agent is the compound $[(Me_3SiO)_2SiMe(CH_2)_3]_2N^+Me_2I^-$ wherein Me is methyl.

11. The detergent in accordance with claim 9 including a carrier fluid selected from the group consisting of water, ethanol, isopropanol, butanol, hexanol, propylene glycol, and diethylene glycol.

12. The detergent in accordance with claim 11 in which the detergent includes at least one surfactant selected from the group consisting of anionic and nonionic surfactants.

13. The detergent in accordance with claim 12 in which the ratio between the anionic surfactant and the nonionic surfactant is from about one to one to from about three to one.

14. The detergent in accordance with claim 13 in which the detergent includes on a weight basis about 0.5 to 5.0 percent of the silicone fabric softening agent.

15. The detergent in accordance with claim 14 in which the silicone is employed in an amount of about 0.05–0.3 percent by weight based on the weight of fabrics being treated.

16. In a laundry detergent having fabric softening properties and including at least one fabric softening agent, the improvement comprising a silicone fabric softening agent having the formula $$[(R_3SiO)_2-SiR-(CHR'')_a]_2N^+R'_2X^-$$

wherein R is an alkyl radical having one to six carbon atoms; R' is an alkyl or aryl radical having one to eighteen carbon atoms; R" is hydrogen or R'; X is chloride, bromide, iodide, nitrate, or $RSO_4^-$; and a is an integer having a value from one to ten.

17. The detergent of claim 16 in which the fabric softening agent is the compound $[(Me_3SiO)_2SiMe(CH_2)_3]_2N^+Me_2I^-$ wherein Me is methyl.

18. The detergent in accordance with claim 16 including a carrier fluid selected from the group consisting of water, ethanol, isopropanol, butanol, hexanol, propylene glycol, and diethylene glycol.

19. The detergent in accordance with claim 18 in which the detergent includes at least one surfactant selected from the group consisting of anionic and nonionic surfactants.

20. The detergent in accordance with claim 19 in which the ratio between the anionic surfactant and the nonionic surfactant is from about one to one to from about three to one.

21. The detergent in accordance with claim 20 in which the detergent includes on a weight basis about 0.5 to 5.0 percent of the silicone fabric softening agent.

22. The detergent in accordance with claim 21 in which the silicone is employed in an amount of about 0.05–0.3 percent by weight based on the weight of fabrics being treated.

* * * * *